(12) United States Patent
Materi

(10) Patent No.: US 8,551,629 B2
(45) Date of Patent: Oct. 8, 2013

(54) PHOTOELECTROMETHANOGENIC MICROBIAL FUEL CELL FOR CO-GENERATION OF ELECTRICITY AND METHANE FROM CARBON DIOXIDE

(75) Inventor: Wayne Paul Materi, Edmonton (CA)

(73) Assignee: Carbonitum Energy Corporation, Edmonton (CA)

( * ) Notice: Subject to any disclaimer, the term of this patent is extended or adjusted under 35 U.S.C. 154(b) by 395 days.

(21) Appl. No.: 13/149,119

(22) Filed: May 31, 2011

(65) Prior Publication Data

US 2011/0300411 A1 Dec. 8, 2011

Related U.S. Application Data

(60) Provisional application No. 61/349,974, filed on May 31, 2010.

(51) Int. Cl.
*H01M 8/16* (2006.01)
(52) U.S. Cl.
USPC ............... 429/2; 429/401; 435/167; 435/168
(58) Field of Classification Search
USPC ............................. 429/2, 401; 435/167, 168
See application file for complete search history.

(56) References Cited

U.S. PATENT DOCUMENTS

2009/0317882 A1* 12/2009 Cheng et al. ............. 435/167
2010/0304458 A1* 12/2010 Bombelli ................. 435/168

OTHER PUBLICATIONS

Powering Microbes with Electricity: direct electron transfer from electrodes to microbes, Lovely, Derek, 2010, Society for applied microbiology and Blackwell Publishing, p. 27-35.*
Microbial Electrosynthesis: Feeding Microbes Electricity to Convert Carbon Dioxide and Water to Multicarbon Extracellular Organic Compounds, Nevin et al. May 25, 2010, ASM, vol. 1, p. 1-4.*

* cited by examiner

*Primary Examiner* — Ula C Ruddock
*Assistant Examiner* — Frank Chernow
(74) *Attorney, Agent, or Firm* — Gowling Lafleur Henderson LLP

(57) ABSTRACT

A photoelectromethanogenic microbial fuel cell apparatus for processing a carbon dioxide flow into electricity and methane. The apparatus comprises: (a) a photosynthetic microbial fuel half-cell component having an electron-conductive anode and a photosynthetic microbial culture for converting light and water into oxygen, protons and electrons; (b) an electromethanogenic microbial fuel half-cell component having an electron-conductive cathode and a methanogenic microbial culture for converting a flow of carbon dioxide into methane using electrons and protons produced in the photosynthetic microbial fuel half-cell; (c) an electrical coupling interconnecting the two microbial fuel half-cells; and (d) an ionic coupling with an ionic separator interconnecting the two microbial fuel half-cells for selectively transporting ions between the microbial fuel half-cell components. A photobiological integrated carbon capture and recycle technology comprising a photoelectromethanogenic microbial fuel cell apparatus for converting carbon dioxide and water vapor captured from gas streams from a gas-emitting facility, into electricity and methane.

13 Claims, 6 Drawing Sheets

PHOTOELECTROMETHANOGENIC MICROBIAL FUEL CELL FOR CO-GENERATION OF ELECTRICITY AND METHANE FROM CARBON DIOXIDE

TECHNICAL FIELD

The present invention relates to equipment and systems for the capture and recovery of carbon dioxide from waste gas streams. More particularly, the present invention pertains to equipment, systems and processes for concurrent capture and recovery of carbon dioxide from waste gas streams with co-generation of electricity and methane from the recovered carbon dioxide. Even more particularly, the present invention relates to the adaptation and combination of photomicrobial fuel cells and electromethanogenic devices and processes to accomplish the desired cogeneration of electricity and methane from the recovered carbon dioxide.

BACKGROUND OF THE INVENTION

Greenhouse gases (GHGs) generally comprise carbon dioxide that is produced primarily from combustion of fossil fuels. The accumulation of GHGs represents a significant threat to global climate stability. Atmospheric carbon dioxide has increased from about 280 ppm in the early 1800s to over 380 ppm in the early 2000s. The 2005 Intergovernmental Panel on Climate Change (IPCC) special report stated that global carbon dioxide ($CO_2$) emissions from fossil fuel-based, large stationary sources (i.e., greater than 0.1 million tonnes of $CO_2$ per year) totaled around 13.4 gigatonnes annually. Fossil fuels responsible for these emissions consisted of 60% coal, 11% natural gas (NG), 7% fuel oil, and a mix of others.

Although numerous strategies have been assessed for capturing and sequestering $CO_2$ from flue gases, the most common high-volume through-put industrial systems typically route flue gases upward through vertical columns that have been provided with screens and/or packing materials over which amine-containing solvent solutions are flowed. The large surface areas of the screens and/or packings facilitate chemical reactions between the amine-containing solvents and the flue gas constituents, which usually are $CO_2$, oxygen ($O_2$), nitrogen ($N_2$), nitrogen dioxide ($NO_2$), sulfur dioxide ($SO_2$) and fly ash of inorganic oxides. The chemical reactions result in primarily of the $CO_2$ component of these flue gas constituents, into the solvent solutions. The solvent solutions containing absorbed $CO_2$ are transferred to equipment that strip the absorbed gaseous flue gas constituents from the amine-containing solvents. This process recharges the amine-containing solvents which are subsequently recycled to the top of the vertical columns where they are reused.

A major problem with such systems however, is that flue gas constituents such as $O_2$, and $SO_2$ may participate in reactions with the amines, particularly at high amine regeneration temperatures, eventually leading to chemical degradation of the amines. Consequently, high amine costs, due to continual replacement of degraded solvents, are commonly associated with such $CO_2$ capture and sequestration systems. Compounding these problems is the high solubility of $SO_2$ in the solvent solutions that are commonly used in combination with amines. $SO_2$ often remains associated with the regenerated solvent solutions when they are re-circulated back into the flue gas-routing columns wherein they subsequently induce corrosion of the packing materials and foaming of the degradation products. Attempts to ameliorate these problems include the addition of degradation inhibitors and/or scavengers, but these approaches have only achieved moderate success.

Other commercial approaches for recovering and sequestering $CO_2$ from waste gas streams include scrubbers containing activated charcoal. Activated charcoal is particularly useful for capturing and adsorbing $CO_2$ from waste gas streams. However, after certain periods of use, the activated charcoal becomes saturated with $CO_2$. The saturated activated charcoal must then be replaced or alternatively, be recharged by purging with air streams containing low $CO_2$ levels. Consequently, scrubbers comprising activated charcoal are not suitable for many industrial applications, and additionally, are burdened with high maintenance costs.

The recovered $CO_2$ must then be compressed, transported and injected into depleted oil or gas reservoirs or into subterranean saline aquifers. Compression as high as 3500 psi is common, requiring substantial energy from the common grid or directly from the emitting facility. Combined with the energy required to regenerate chemical absorbents, this process often imposes a parasitic power loss of over twenty percent on the emitting facility, resulting in relatively poor economic justification of carbon capture and sequestration processes.

Other strategies for capturing and sequestering $CO_2$ from atmospheric environments in order to improve air quality in buildings and/or outdoor spaces have employed biological processes. For example, plants absorb and convert copious amounts of $CO_2$ into sugars that are used to fuel the development of plant biomass in the forms of celluloses, hemicelluloses, oligosaccharides and polysaccharides. Rapidly growing and photosynthesizing plants have been deployed for $CO_2$ capture and sequestration in vertical plant walls installed on exteriors and interiors of buildings, and in marshland cropping systems. However, such systems are not suitable for capturing and sequestering $CO_2$ from flue gases. Another problem with plant-based systems is the disposal of the vegetative matter at the end of the plant growth cycles.

Another biological strategy for the capture and sequestration of $CO_2$ pertains to the use of cyanobacter microorganisms, commonly referred as photosynthetic blue-green algae. Cyanobacteria are commonly grown in pools or tanks for capture and sequestration of $CO_2$ from atmospheres. Unfortunately, such systems are not suitable for capturing and sequestering $CO_2$ from industrial flue gases.

SUMMARY OF THE INVENTION

Exemplary embodiments of the present invention relate to a photoelectromethanogenic fuel cell apparatus that uses photonic energy for simultaneous production i.e. co-generation, of electricity and methane from $CO_2$. An exemplary embodiment of the apparatus comprises a photosynthetic microbial fuel half-cell component (PMFhC) coupled to an electromethanogenic microbial fuel half-cell component (EMFhC). According to one aspect, the PMFhC component is provided with selected and/or genetically modified cyanobacteria which photosynthetically split water molecules into free electrons, protons and oxygen. The electrons are collected from the PMFhC component and are conveyed to the EMFhC component by wire transmission. The protons in the PMFhC component are dissolved in the growth medium and are transferred across a proton exchange membrane (PEM) to a growth medium provided in the EMFhC component. The oxygen is removed from the medium and can be collected or alternatively, released to the atmosphere. According to another aspect, the EMFhC component is provided with selected and/or genetically modified methanogenic bacteria that use the electrons and protons received from the PMFhC component for biochemical reduction of $CO_2$ to methane.

Other exemplary embodiments of the present invention relate to systems comprising one or more sets of coupled PMFhC components and EMFhC components that receive $CO_2$ captured from flue gases emitted by stationary plants that combust fossil fuels in their operations. Exemplary embodiments of the systems are generally configured for receiving flue gases which are then cooled for separation and recovery of water from the other flue gas constituents exemplified by $CO_2$, $O_2$, $N_2$, $NO_2$, $SO_2$, and fly ash of inorganic oxides among others. According to one aspect, the recovered water may be routed to the PMFhC component for photosynthetic splitting into electrons, protons and oxygen. According to another aspect, the gas constituents are then bubbled (e.g. by micro-sparging) through suitable microbial liquid growth medium provided in the EMFhC component. The differences in the relative solubilities of the gas constituents will result in most of the $CO_2$ and some of the $O_2$ being solubilized into the liquid growth medium. According to another aspect, the $CO_2$ and $O_2$ loaded liquid growth medium is passed through a gas exchange device (using methane from the EMFhC component as a counter-flow gas) to remove residual oxygen before the microbial gas solution is transferred into EMFhC component. According to yet another aspect, the methane produced in the EMFhC component is recyclable to the stationary plants emitting the flue gases, wherein the methane can be used to generate as a fuel thereby offsetting some of stationary plants' requirements for fossil fuels.

DESCRIPTION OF DRAWINGS

The present invention will be described in conjunction with reference to the following drawing, in which.

DETAILED DESCRIPTION OF THE INVENTION

Figure 1:
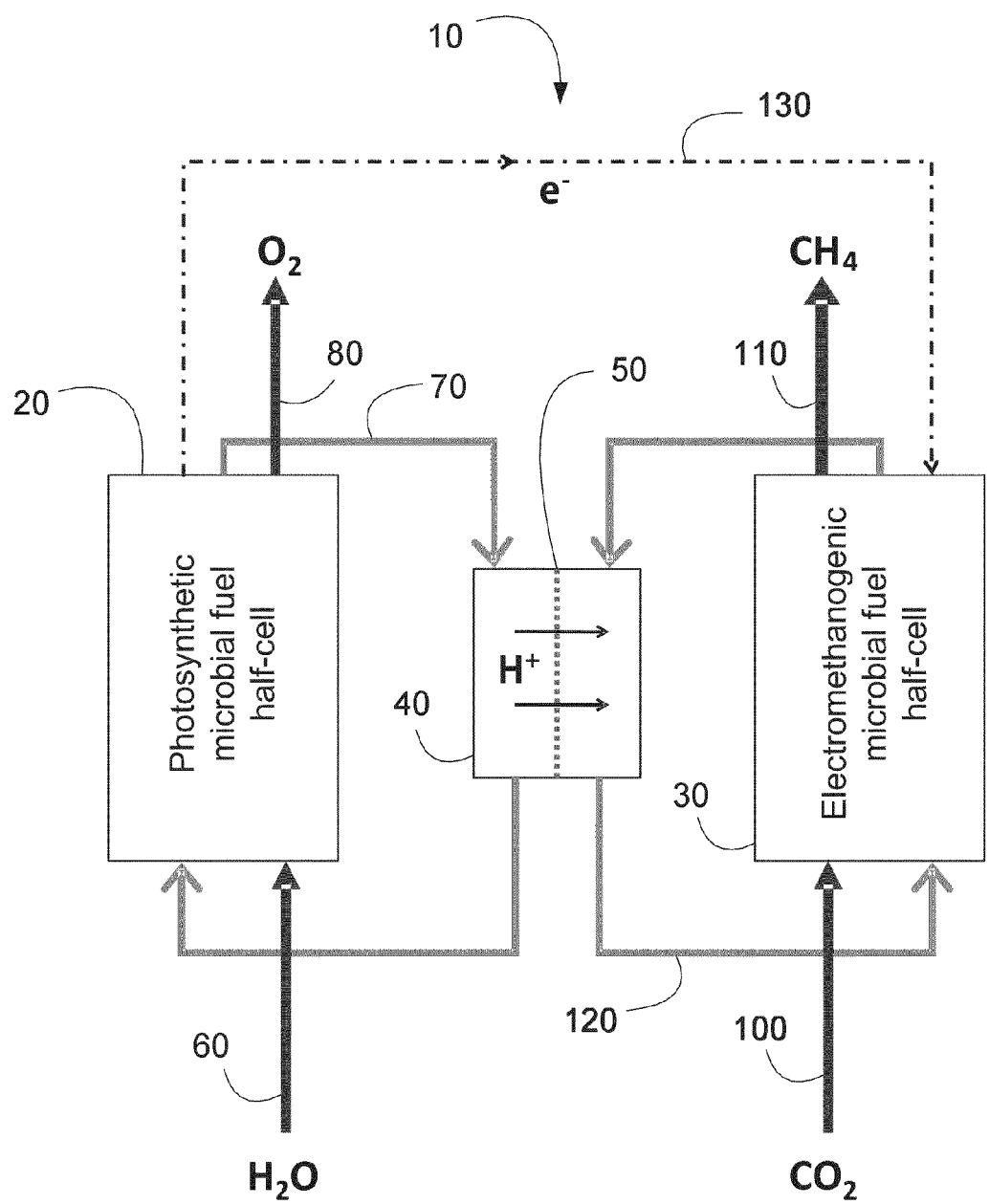
FIG. 1 is a schematic drawing showing an exemplary photoelectromethanogenic fuel cell, comprising an exemplary photosynthetic microbial fuel half-cell (PMFhC) coupled to an exemplary electromethanogenic microbial fuel half-cell (EMFhC) in a configuration for the simultaneous production of electricity and chemical reduction of carbon dioxide to methane.

Exemplary embodiments of the present invention relate to a photoelectromethanogenic fuel cell apparatus that uses photonic energy for simultaneous production i.e. co-generation, of electricity and methane from $CO_2$. An exemplary embodiment of the apparatus comprises a photosynthetic microbial fuel half-cell (PMFhC) component coupled to an electromethanogenic microbial fuel half-cell (EMFhC) component.

As growing organisms metabolize glucose, they separate negative and positive charges. Positive charges are collected in protons which form an electrochemical gradient across plasma membranes, while negative charges are accumulated within specific metabolic intermediates. These charges can be collected and utilized under appropriate conditions. Microbial fuel cells (MFCs) are electrically coupled pairs of chambers (called half-cells) that produce electricity directly from metabolic reduction-oxidation (redox) reactions. Typically, electron-producing oxidation reactions take place in one half-cell where glucose-metabolizing microorganisms transfer electrons to a conductive anode. Electrons (e–) may be transferred to the anode directly through conductive nanowires or through electron shuttle intermediates. The anode is connected by a wire to a cathode in an adjacent half-cell. Protons carrying the separated positive charge in solution (H+) are transferred from the oxidation half-cell to the reduction half-cell across a proton exchange membrane (PEM), cation exchange membrane (CEM), anode exchange membrane (AEM) or via a salt bridge.

The protons and electrons from the oxidation half-cell can be utilized in the reduction half-cell to biochemically reduce a number of potential terminal electron acceptors. In many experimental MFCs, for example, ferricyanide or Manganese (IV) is used as the terminal electron acceptor. However, most practical MFCs use atmospheric oxygen as the terminal electron acceptor. The cathode may either be immersed in highly oxygenated water or may be in a gas electrode contacting free oxygen. Oxygen-reducing electrodes are typically made of a catalyst, such as platinum or graphite, to reduce the required activation energy of the reduction reaction.

Because MFCs utilize sugars and other organic foods in the anodic half-cell, their use has mainly been investigated in the treatment of wastewater. Electricity produced by wastewater MFCs can be used to offset the electricity requirements of other processes in the treatment plant. Bacterial cultures at either the anode or cathode for wastewater treatment MFCs often consist of more than a single bacterial strain to fully utilize all available nutrients.

A photosynthetic microbial fuel cell (PMFC) replaces the glucose oxidation reactions in the anode reactor of a typical MFC with the light-dependent water-splitting reactions of photosynthetic organisms such as algae and/or cyanobacteria. The early steps of photosynthesis use light energy to split water into free electrons, protons and oxygen gas. The electrons and protons of typical photosynthesizing organisms are naturally used to produce organic chemical reductants (e.g. NADPH) and internal energy stores (e.g. ATP). However, in the presence of an appropriate anode, electrons can be collected and transferred to an attached cathode. Protons released by photosynthesis can be transferred from the anodic half-cell to the cathodic half-cell across a PEM. As with the MFC, the protons and electrons are combined in the cathode chamber to chemically reduce free oxygen to water. Again, the cathode may either be immersed in highly oxygenated water or may be in a gas chamber contacting free oxygen.

Recently other reactions at the cathode have been investigated for use in MFCs. For example, it is suitable to use methanogenic archaea as electron acceptors or biocathodes. Most methanogens are obligate anaerobes that provide an alternative $CO_2$ fixation pathway to the Calvin cycle through biochemical reduction to methane. Reducing potential normally comes either directly from hydrogen gas or indirectly from acetate. Recently, methanogens have been shown to be capable of directly utilizing protons and electrons in carbon dioxide reduction biochemistry. This process is known as electromethanogenesis.

Figure 2:
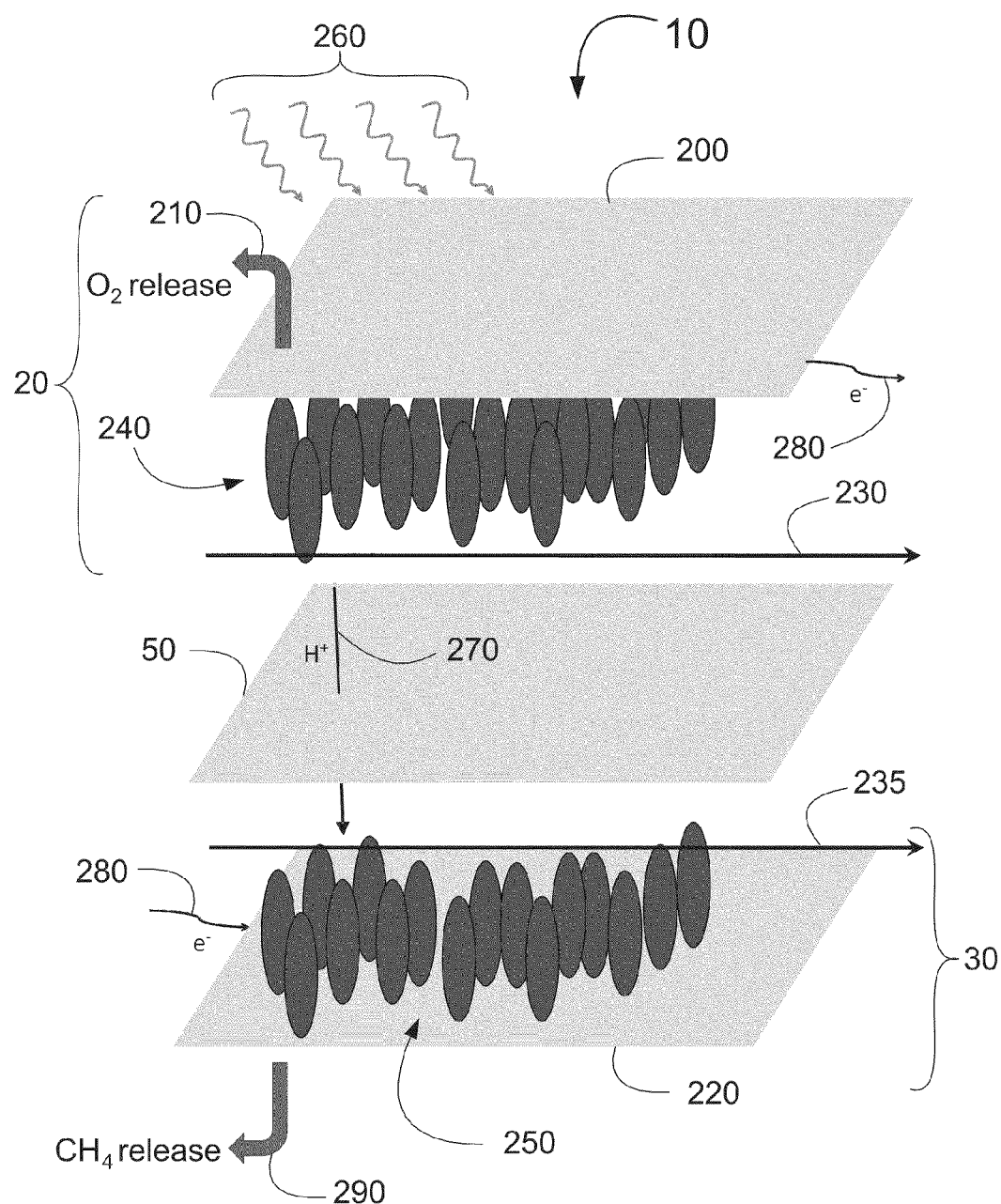
FIG. 2 is a perspective drawing of an exemplary unit cell from FIG. 1 with its side walls removed for illustration of its internal operation, said unit cell consisting of a PMFhC cyanbacterial biofilm on a conductive, transparent anode and an EMFhC methanogen biofilm on a conductive cathode, with the electrodes connected by a conductor, and both half-cells sharing a common Proton Exchange Membrane (PEM)

FIGS. 1 and 2 show an exemplary photoelectromethanogenic fuel cell apparatus 10 according to one embodiment of the present invention, comprising a "photosynthetic microbial fuel half-cell" 20, referred to herein after as a "PMFhC component", coupled to an "electromethanogenic microbial fuel half-cell" 30, referred to hereinafter as an "EMFhC component", for the simultaneous production i.e., co-generation of electricity and methane from $CO_2$ recovered from gas streams exemplified by combustion flue gases and the like. The PMFhC component 20 includes a biofilm of cyanobacteria 240 on the illuminated anodic surface 200 for production of free electrons 280 and dissolved protons 270 by photolysis of water through the light reactions of photosynthesis. The electrons 280 are collected by the anode in the PMFhC component and transmitted by wire 130 to a conductive cathode 220 in the EMFhC component 30. The protons 270 are transported in solution within the PMFhC component medium 230 and circulated for selective transfer into the circulating EMFhC component medium 235, via a suitable bridging device 50 exemplified by a proton exchange membrane (PEM), a cation exchange membrane (CEM), an anion exchange membrane (AEM), an ultrafilter membrane, a salt bridge, and the like. Numerous suitable materials for each of these are well known in the art. Free electrons 280 and protons 270 are produced by photosynthesis and collected from the PMFhC component 20 when the cyanobacteria 240 contained therein are illuminated 260. The electrons 280 and protons 270 are utilized by the cathodic biofilm of methanogenic bacteria 250 in the EMFhC component 30 to reduce flue gas carbon dioxide 100 to methane 290.

According to one exemplary embodiment, the PMFhC component 20 and EMFhC component 30 can be combined in a unit cell 10 with the PMFhC cyanbacterial biofilm 240 on a conductive, transparent anode 200 and the EMFhC methanogenic biofilm 250 on a conductive cathode 220, with the electrodes connected by a conductor, and both half-cells sharing a common Proton Exchange Membrane 50 (PEM) across which protons 270 produced by the PMFhC component 20 are transported into the EMFhC component 30.

According to an exemplary embodiment, the PMFhC component may be a chamber with an external surface exposed directly to natural or artificial light. The chamber may have a planar, cylindrical, cuboid or other simple or complex geometry which maximizes the biofilm surface area exposed to the external light source. FIG. 2 shows a perspective view of a single PMFhC component within an exemplary unit cell with side walls removed for illustration. The top plate of the PMFhC component 20 is made from electrically-conductive, transparent glass or plastic 200, while the bottom plate and side plates (not shown in FIG. 2) are opaque or reflective. Methods for producing such electrically conductive, transparent surfaces are known in the art and several products are available commercially from Evaporated Coatings Inc. (Willow Grove, Pa., USA), Less EMF Inc. (Albany, N.Y., USA), VisionTek Systems Ltd. (Chester, Cheshire, UK). Suitable cyanobacteria cultured in the PMFhC component 20 form a biofilm 240 on the inner surface of the transparent conductive glass 200 or polymer. Electrons 280 produced through photosynthesis are conducted from the cyanobacterial culture 240 to the conductive inner surface of the top plate 200 and then to a wire or other conductive material 130 interconnecting the PMFhC component 20 and the EMFhC component 30. The entire PMFhC component is filled with cyanobacteria culturing medium 230 which enters on one side of the PMFhC component and exits from the other side of the PMFhC component. Dissolved protons 270 produced during photosynthesis are transported from the PMFhC component 20 to the EMFhC component 30. Gaseous oxygen 210 produced during photosynthesis forms bubbles in the PMFhC component 20 and is released through a valve (not shown).

Figure 4:
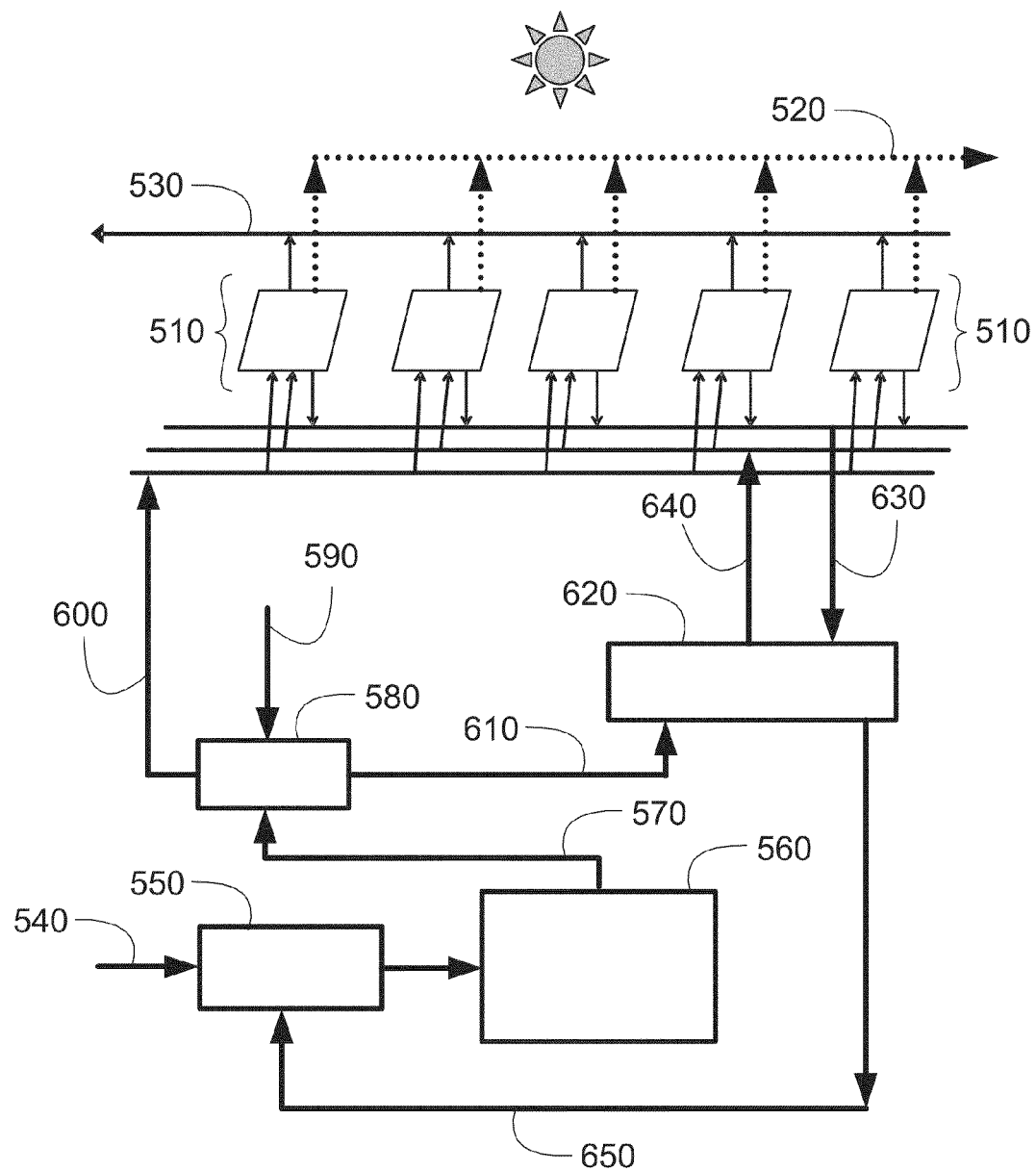
FIG. 4 is a schematic drawing showing an exemplary integration of an exemplary array of interconnected photoelectromethanogenic fuel cells into a system for capturing flue gases produced by an industrial-scale cogeneration power plant for production of methane that is cycled back into the power plant.

According to another exemplary embodiment, external solar or artificial light can be captured by a number of methods known in the art, including but not limited to external arrays 510 of holographic planar concentrator film arrays of reflectors, fresnel lens collectors and total internal reflection films, and routed through a light waveguide or fiber optic cable to the interior of the PMFhC component 500 (FIG. 4). Light monitoring and control devices can be incorporated into the transmission channels to ensure that light irradiation of optimal intensity and frequency to support photosynthesis in cyanobacteria, is transmitted to an internal light distribution component of the interior of the PMFhC component. In this embodiment, suitable cyanobacteria could form a biofilm on a separate anode which is illuminated by the light which has been guided into the interior of the PMFhC component and distributed evenly therein. In another embodiment, suitable cyanobacteria could form a biofilm directly on the illuminated surface of said internal light distribution component, which could be coated with a transparent, conductive material to form the PMFhC anode.

The characteristics of suitably bred, selected and/or genetically modified cyanobacteria for use in the PMFhC modules of the present invention include but are not limited to the following: (1) ability to form biofilms on the anode surfaces of the PMFhC component; (2) efficiently conduct electrons produced by the light reactions of photosynthesis to the anode throughout the entire thickness of said biofilm; (3) efficiently export to the medium protons produced by the light reactions of photosynthesis; (4) grow, divide and reproduce minimally so as to greatly reduce the number of new cells formed on the biofilm or in solution once production of electricity in the PMFhC component commences; (5) unicellular cyanobacteria such as those exemplified by *Synechocuccus* sp., *Synechocystis* sp., *Prochlorococcus* sp. and the like, and/or filamentous cyanobacterial species exemplified by *Anabaena* sp., *Nostoc* sp., *Trichodesmium* sp. and the like.

FIG. 2 shows a perspective view of an EMFhC component 30 within an exemplary unit cell 10 with side walls removed for illustration. Methanogens form a biofilm 250 on the inner surface of the bottom conductive glass or polymer 220 in the EMFhC component 30. Electrons 280 produced in the PMFhC component 20 are conducted by wire 130 to the conductive inner surface 220 of the EMFhC component 30 while protons 270 are transported in solution across a suitable bridging device 50 (also refer to FIG. 1). Electrons 280 and protons 270 transported to the EMFhC component 30 from the PMFhC component 20, are utilized by methanogenic archaea (methanogens) 250 contained in the EMFhC component 30. The methanogens 250 combine the electrons 280 and protons 270 to biochemically reduce the captured flue gas carbon dioxide 100 to methane gas 110, 290.

The characteristics of a preferred selected and/or bred and/or genetically modified methanogen include but are not limited to the following: (1) ability to form a biofilm on the surface of the EMFhC component cathode; (2) efficiently conduct electrons from the cathode throughout the entire thickness of said biofilm to the methanogens; (3) efficiently import from the EMFhC component medium protons produced in the PMFhC component and transported from there; (4) grow, divide and reproduce minimally so as to greatly reduce the number of new cells formed on the biofilm or in solution once production of electricity in the PMFhC component commences; (5) both mesophilic (moderate temperature) and thermophilic (higher temperature) methanogenic archaea exemplified by *Methanobacteriales* sp., *Methanococcales* sp., *Methanomicrobiales* sp., *Methanosarcinales* sp., *Methanopyrales* sp. and the like, and in particular, autotrophic species from these orders that require only $CO_2$ as their sole carbon source.

The exemplary apparatus described herein can be incorporated into a system to convert $CO_2$ recovered from waste gas streams, to methane gas. Suitable waste gas streams and flue gases can originate from combustion of fossil fuels exemplified by natural gas, coal or fuel oil. This includes electricity generation or co-generation plants along with other similar industrial and residential facilities. In addition, $CO_2$ produced by hydrocarbon-utilizing fuel cells (whether based on proton exchange membrane, solid oxide or other technologies) can also be recycled according to some exemplary embodiments of the present invention. The methane derived from $CO_2$ with the exemplary apparatus can subsequently be recycled to the emitting facility for further energy production (off-setting the required fossil fuel input) or alternatively, can be compressed and stored for future use. The electricity is mostly used in the EMFhC component but may also be used in local electrical circuits for other work or returned to the common electrical distribution grid.

Figure 3:
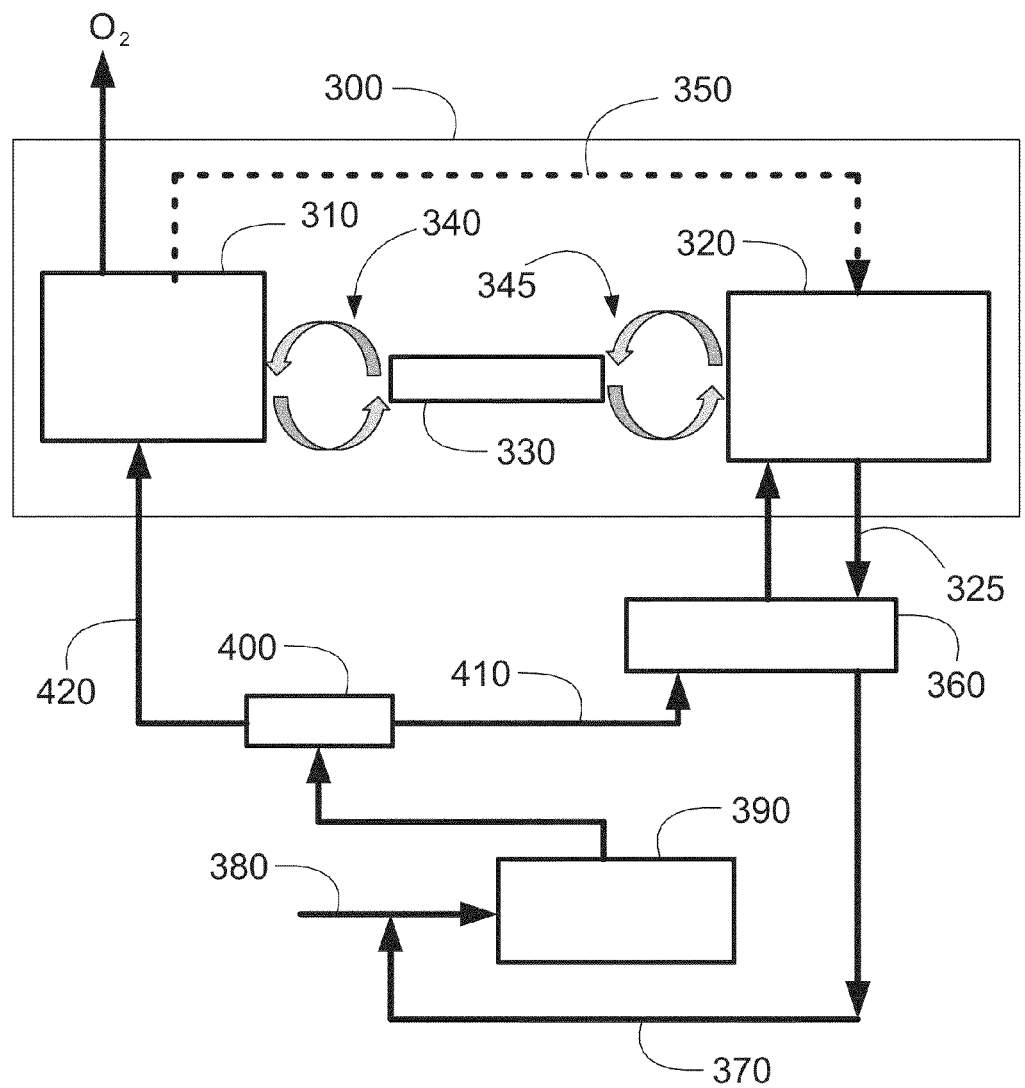
FIG. 3 is a schematic flowchart illustrating an exemplary use of the photoelectromethanogenic fuel cell shown in FIG. 1, for co-generation of electricity and methane using $CO_2$ and water vapor captured from the flue gas of an exemplary natural gas combustion facility, through a system referred to herein as a "Photobiological Integrated Carbon Capture and Recycling Technology" (PICCART) system.

FIG. 3 shows a schematic flowchart illustrating the use of an exemplary photoelectromethanogenic fuel cell apparatus 300 of the present invention for the co-generation of electricity and methane from $CO_2$ recovered from flue gases produced by a natural gas (NG) fueled stationary plant 390 by combustion of a natural gas and air mixture 380. Flue gases produced by the NG-fueled stationary plant 390 are cooled in a condenser 400 for removal of water vapors as condensed water 420. The condensed water 420 is conveyed to the PMFhC component 310 where cyanobacterial films use photonic energy to power photosynthesis resulting in the production of free electrons, dissolved protons and oxygen. The oxygen produced in the PMFhC component 310 is released to the atmosphere. Electrons from the PMFhC component 310 are conveyed to the EMFhC component 320 by wire transmission 350. The liquid media 340 from the PMFhC component 310 and liquid media 345 from the EMFhC component 320 are circulated over a proton exchange membrane (PEM) 330, wherein protons are transferred from the PMFhC component media 340 to the EMFhC component media 345. Any oxygen dissolved in the PMFhC component 310 can be first removed through a degassing process, if necessary to reduce the concentration of oxygen transmitted to the EMFhC media 345. In the EMFhC component 320, electrons and protons from the PMFhC component 310 are consumed by methanogenic archaeal biofilms to reduce $CO_2$ in the de-watered flue gases 410 to methane 325. Flue gas carbon dioxide is first dissolved in the EMFhC component medium, then any residual dissolved oxygen can be removed by exchange (for example, in a hollow fiber gas exchange device 360) with a counter-flow of methane 325 from the EMFhC component 320. The methane output 370 from the EMFhC component 320 can then be recycled to the NG-fueled stationary plant 390 for further combustion and power generation.

The flue gases may comprise 2-8% $CO_2$, 9-20% $CO_2$, 20-80% $CO_2$, along with water vapor, nitrogen, oxygen (preferably less than 3%), carbon monoxide, sulfur dioxide (preferably less than 0.1%) and other residual gases. The flue gases are cooled and water vapors therein are removed by condensation and recovery. The condensed water is cooled to match the optimal process temperature for formation and functioning of cyanobacterial biofilms in the PMFhC components. The recovered condensed water is incorporated into the PMFhC component to supply $H_2O$ for production of free electrons, dissolved protons and oxygen gas through photosynthesis.

In an exemplary embodiment of said system, pre-processing of said flue gases prior to transfer into the EMFhC component can include moderate pressurization and passage through a microporous sparger immersed in electromethanogenesis medium to optimize dissolution of flue gas carbon dioxide using methods known in the art. Undissolved gases can be recirculated back through the microsparger or released back to the atmosphere upon excessive pressure build-up in the headspace. The medium containing dissolved gases can be passed through a gas exchange device where the counter flow is methane gas from the EMFhC component. This will reduce dissolved oxygen in the electromethanogenesis medium by transferring it into the methane stream prior to recycling it back to the plant.

In one embodiment, continuous operation of the process is achieved by using an artificial light source when sunlight is not available. In this embodiment, excess electricity may be produced when sunlight is available and transmitted to the general electric distribution grid. This could partially offset the electricity taken from the grid for artificial light production when sunlight is not available.

In another embodiment, electrons produced during sunlight hours may be stored locally (e.g. in batteries or by other methods well known in the art) while protons may be stored locally in a buffer solution. When sunlight is unavailable, said stored electrons and protons may be transmitted to the EMFhC component for direct utilization.

In one embodiment, the medium from the PMFhC component is degassed by one of the methods well-known in the art to remove dissolved oxygen prior to exposure to the proton exchange membrane.

In another embodiment, the dissolved oxygen in the PMFhC component medium is removed by gas exchange using methane from the EMFhC component as a counter-flow gas. Methods and devices for said gas exchange are well known in the art and a number of these are commercially available.

Another exemplary embodiment of the present invention pertains to a system capable of processing flue gas from a large (e.g., >0.1 Mtonnes/year) stationary carbon dioxide emitter that includes a collection of exemplary photoelectromethanogenic fuel cell devices according to the present invention, arrayed in a manner that can optimize light capture directly from solar or artificial sources. For reference purposes, such systems can be referred to as "Photobiological Integrated Carbon Capture and Recycle Technology" (i.e., PICCART) systems. FIG. 4 shows an exemplary embodiment of a PICCART system wherein an array of photoelectromethanogenic fuel cell devices 510 interconnected to process the flue gases of a natural gas cogeneration power plant 560. Light irradiation illuminating the array of photoelectromethanogenic fuel cell devices 510 drives photosynthesis by the photosynthesizing biofilms in the PMFhC components (not shown) to produce electrical current 520 and oxygen 530. Cooled water 600 recovered from the flue gases 570 by the condenser unit 580 is combined with residual water 590 from the electromethanogenic reactions in the EMFhC components (not shown) in the array of photoelectromethanogenic fuel cell devices 510 and distributed to each individual photoelectromethanogenic device by a series of interconnected pipes. Similarly, processed de-oxygenated flue gases 640 in EMFhC media from the $CO_2$ pre-processing unit 620 of the parallel PICCART process are distributed evenly to each photoelectromethanogenic device in the array 510 through a set of interconnected pipes. Methane produced by the individual photoelectromethanogenic fuel cell devices, is collected and combined by a series of interconnected pipes to be used as an exchange counter-flow gas 630 in the $CO_2$ pre-processing unit 620 and subsequently recycled 650 to the natural gas cogeneration plant combustion unit 560 through a pre-combustion processing unit 550, where it is mixed with incoming fossil fuel natural gas 540 to maintain correct flow to the combustion process.

Figure 5:
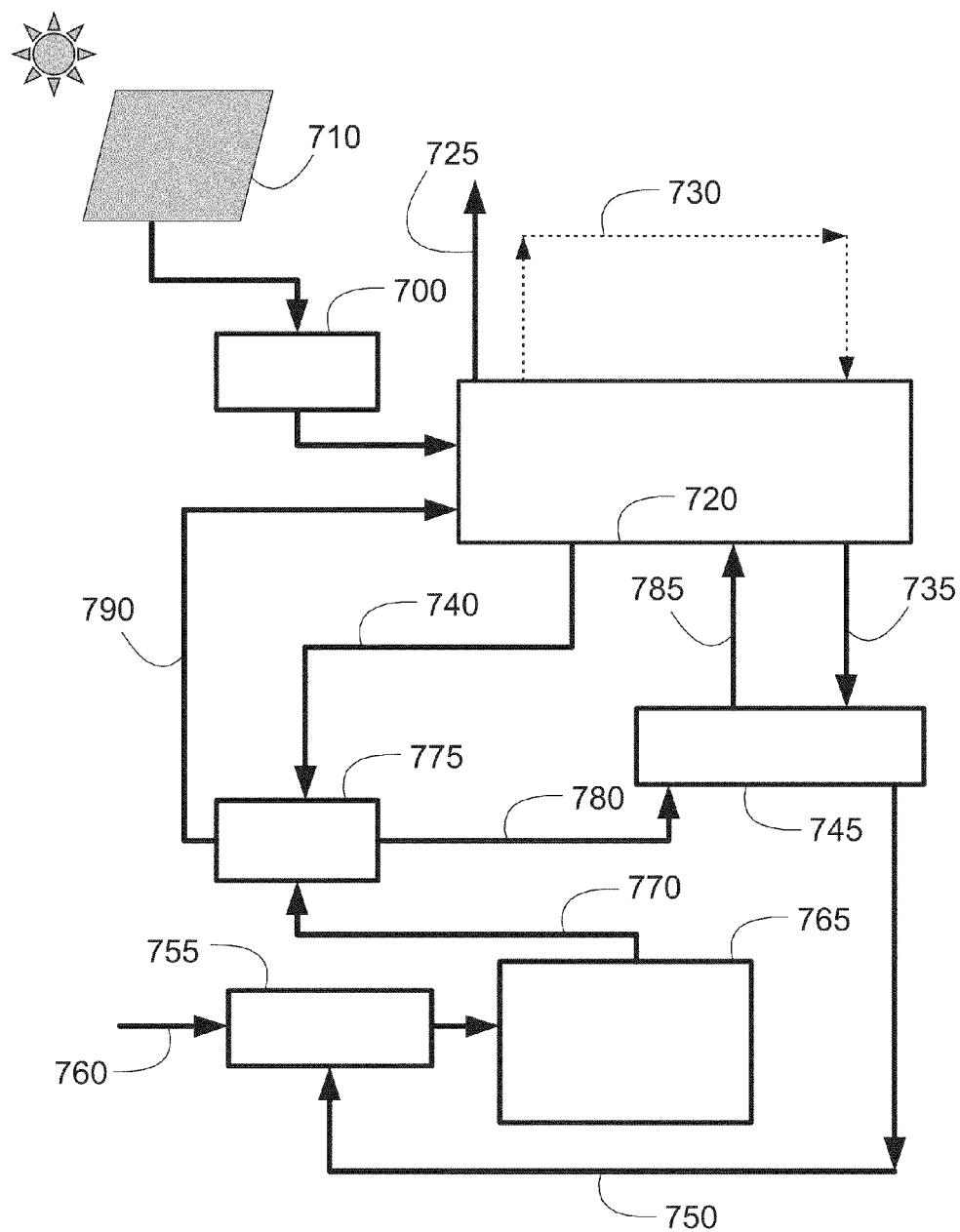
FIG. 5 is a schematic drawing showing irradiation by an external solar energy capture system of an exemplary single large photoelectromethanogenic fuel cell for processing flue gases produced by an industrial-scale cogeneration power plant for production of methane that is cycled back into the power plant.

In another embodiment, a system capable of processing flue gas from a large (i.e., >0.1 Mtonnes/year) stationary carbon dioxide emitter can include a plurality of exemplary photoelectromethanogenic fuel cell devices of the present invention described, wired in a parallel circuit and with interconnected tubing permitting optimal flow of the medium between the separate devices. FIG. 5 shows an exemplary embodiment of a single photoelectromethanogenic fuel cell apparatus 720 to process the flue gases of a natural gas cogeneration power plant 765. Light is collected by a separate light-capture field 710 and processed by passage through a series of lenses, mirrors, guides, sensors and regulators 700 to the PMFhC component (not shown) of a single photoelectromethanogenic fuel cell apparatus 720 to produce electrical current 730 and oxygen 725. Cooled water 790 recovered from the flue gases 770 by the condenser unit 775 is combined with residual water 740 from the electromethanogenic reactions in the EMFhC components (not shown) in the photoelectromethanogenic fuel cell apparatus 720. Similarly, processed de-oxygenated flue gases 785 in EMFhC media from the $CO_2$ pre-processing unit 745 are distributed to the photoelectromethanogenic fuel cell apparatus 720. Methane produced by the photoelectromethanogenic fuel cell apparatus 720 is collected and used as an exchange counter-flow gas 735 in the $CO_2$ pre-processing unit 745 and subsequently recycled 750 to the natural gas cogeneration plant combustion unit 765 through a pre-combustion processing unit 755, where it is mixed with incoming fossil fuel natural gas 760 to maintain correct flow to the combustion process.

In one embodiment of said system, the predominantly methane gas produced in the EMFhC component can be collected and returned to the emitting plant for use therein.

In another embodiment the predominantly methane gas produced in the EMFhC can be collected and pressurized for storage.

EXAMPLE

Figure 6:
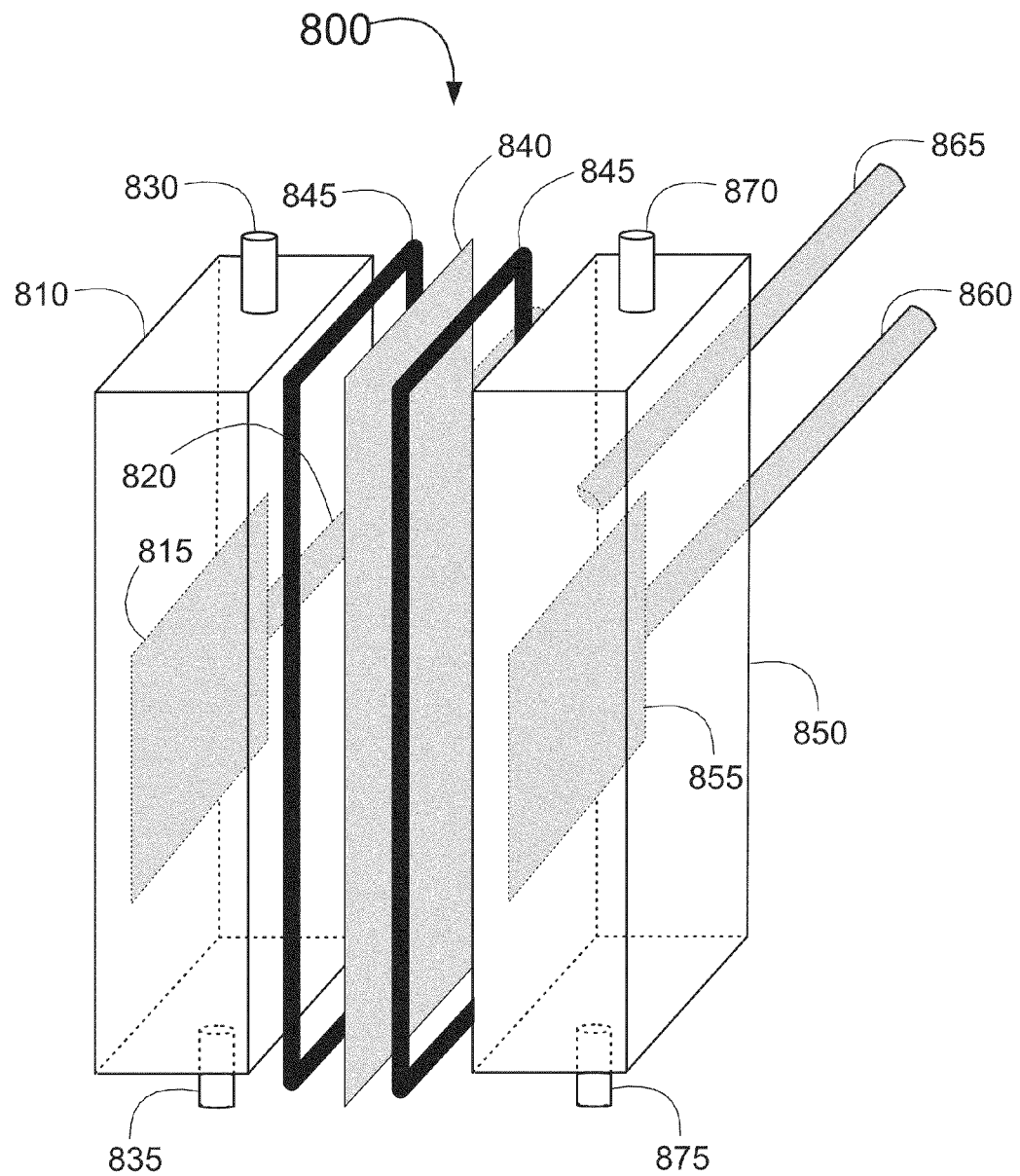
FIG. 6 is a schematic drawing showing an exploded image of an exemplary unit cell, comprising two acrylic boxes with open inner surfaces sandwiching a Nafion Proton Exchange Membrane between butyl rubber gaskets and with attached top and bottom inlet and outtake barbed hose connectors, for media circulation, and with inserted electrodes for conventional three-electrode potentiostat measurement of voltage and current.

An experimental prototype apparatus 800 without microbial biofilms is shown in FIG. 6. The prototype apparatus 800 comprised a single acrylic unit cell of dimensions about 6"×6"×3", made of two acrylic boxes 810, 850 open along the facing sides. The unit cell was assembled by screws drilled through the four corners of each half-cell such that the Proton Exchange Membrane 840 exemplified by Nafion® 117 (Nafion is a registered trademark of E.I du Pont de Nemours and Company Corp., Willmington, Del., USA) was sandwiched between two butyl rubber gaskets 845 and the acrylic half-cells 810, 850. Holes were drilled in the top and bottom of each half cell 810, 850 and barbed polyethylene hose connectors 830, 835, 870, 875 were glued to the acrylic half-cells 810, 850. Polyvinyl-chloride (PVC) tubing exemplified by Nalgene 8000-080 (Nalgene is a registered trademark of Nalge Nunc International Corp., Rochester, N.Y., USA) was used to connect the half-cells to separate acrylic reservoirs containing media or other liquids and, potentially, cyanobacterial cultures (connected to the PMFhC side) or methanogen cultures (connected to the EMFhC side) (not shown). PVC tubing was used to reduce oxygen diffusing into the apparatus 800 through semi-porous tubing; the tubing walls were ⅛" thick. Experiments using silicon peristaltic tubing, circulating cyanobacterial media (BG-11) and methanogen media (ATCC 1043) with resazurin redox indicator demonstrated the absolute importance of using highly oxygen-impermeable tubing such as PVC tubing. Separate inline pumps (Little Giant Pump Company model 1-EA-42) were used to circulate media through each half-cell and its associated reservoir. Reservoirs (not shown) were made of 6"×6"×6" acrylic boxes (⅛" thick) with separate lids, attached by screws and sealed with rubber gaskets. The lids contained two or three holes through which air or $CO_2$ could be introduced into the media through a 0.22 µm filtered line by sparging, or through which instruments, such as a thermometer, pH meter, dissolved $O_2$ probe, etc., could be introduced. Because the methanogen media contained hydrogen sulphide-producing components, the methanogen reservoir was connected to an ammonium hydroxide gas trap and downstream lead acetate indicator paper in a flask. Air was bubbled into the cyanobacteria reservoir driven by an external aquarium air pump. An anode graphite electrode 820 was introduced into a first half cell 810, and a cathode graphite electrode 860 was introduced into the second half-cell through separate holes drilled in orthogonal sides. The anode 820 and the cathode 860 assemblies consisted of platinum wires attached to separated iso-molded graphite plates 815, 855 (#BL001220, The Graphite Store, www.graphitestore.com) using a silver conductive epoxy covered by a regular non-conductive epoxy for additional strength. The platinum wires were threaded through single hole rubber stoppers and the holes filled with rubber cement to prevent media leakage. The acrylic half-cell 850 functioning as the PMFhC cell was provided with an additional electrode hole into which was inserted an AgCl reference electrode 865 threaded through a rubber stopper. The three electrodes were connected to a potentiostat (Digi-Ivy model DY2300) for recording open-circuit potentials (OCPs), amperommetry or cyclic voltammetry (CV) measurements.

In order to properly fill the device with liquid (media or otherwise) and to avoid the creation of air pockets especially in the unit cell, the unit cell was placed with media-circulating intakes and exits in the vertical position as shown in FIG. 6. Liquid was poured directly into the reservoirs (about two liters per reservoir) then the pumps engaged to circulate liquid into the unit cell and back to the reservoirs.

In order to characterize the ability of the Proton Exchange Membrane (PEM) to transport protons (measured by decrease in pH) without transporting oxygen, both reservoirs were filled with 0.1×PBS solution. Anaerobic carbon dioxide was sparged into the EMFhC reservoir and air was sparged into the PMFhC reservoir while pH was measured in the PMFhC reservoir (using a VWR Scientific SB21 pH meter) _and dissolved oxygen (dO) was measured in the EMFhC (using a VWR Symphony SP70D dissolved oxygen meter). If the device functions properly, protons from the dissolution of carbon dioxide in the EMFhC reservoir should be transported across the PEM to the PMFhC reservoir, reducing its pH. At the same time dissolved oxygen in the PMFhC reservoir should not increase dissolved oxygen (dO) content in the EMFhC reservoir. The results are shown in Table 1 and demonstrate that the PEM transports protons from one side to the other without transporting dissolved oxygen the other way. By comparison, Table 2 demonstrates the changes in pH and dissolved oxygen in the same liquid when measured directly in a reservoir sparged with carbon dioxide.

TABLE 1

Inter-chamber transport of protons and dissolved oxygen

| Time (min) | pH (PMFhC) | dO mg/L (EMFhC) |
|---|---|---|
| 0 | 7.05 | 5.3 |
| 5 | 6.64 | 2.2 |
| 10 | 6.45 | 1.3 |
| 15 | 6.19 | 1.1 |
| 20 | 5.95 | 1.3 |
| 25 | 5.80 | 1.4 |
| 50 | 4.27 | 0.6 |
| 90 | 4.21 | 0.7 |

TABLE 2

Intra-chamber pH and dissolved oxygen changes

| Time (min) | pH (EMFhC) | dO mg/L (EMFhC) |
|---|---|---|
| 0 | 7.02 | 4.2 |
| 5 | 4.84 | 3.5 |
| 10 | 4.82 | 2.7 |
| 15 | 4.82 | 2.4 |
| 20 | 4.82 | 2.0 |
| 30 | 4.82 | 1.8 |

Those skilled in these arts will understand that many embodiments may be made of the invention disclosed herein without departing from the scope thereof. Accordingly, it is to be understood that all matter herein set forth is to be interpreted as illustrative. Certain features and subcombinations that are of utility may be employed including substitutions, modifications, and optimizations, as would be available expedients to those of ordinary skill in the art. It will be understood that while certain embodiments are described herein, all modifications and further utilizations of the principles of these embodiments, as would occur to those ordinarily skilled in the art to which the process relates, are contemplated as being a part of the process.

The invention claimed is:

1. A system for concurrently processing a carbon dioxide flow from a gas stream into electricity and methane, the system comprising:
a first apparatus for receiving therein the gas stream and recovering therefrom (i) a flow of condensed water, and (ii) a gas flow comprising carbon dioxide;
an operating photoelectromethanogenic microbial fuel cell apparatus for processing a carbon dioxide flow into electricity and methane, the apparatus comprising:
a photosynthetic half-cell component for culturing therein photosynthetic microorganisms, said photosynthetic half-cell component provided with a light-receiving element and an electron-conductive anode;
an electromethanogenic half-cell component for culturing therein methanogenic microorganisms, said electromethanogenic half-cell component provided with an electron-conductive cathode;
an electrical coupling interconnecting the photosynthetic half-cell component and the electromethanogenic half-cell component; and
an ionic coupling interconnecting the photosynthetic half-cell component and the electromethanogenic half-cell component, said ionic coupling provided with an ion separator;
wherein (iii) the photosynthetic half-cell component is provided with a circulating liquid medium commingled with a portion of the flow of condensed water from the first apparatus and is culturing therein photosynthetic microorganisms thereby producing oxygen, protons and electrons, and (iv) the electromethanogenic half-cell component is provided with a circulating liquid medium commingled with a portion of the gas flow comprising carbon dioxide from the first apparatus and a portion of the protons and electrons produced in the photosynthetic half-cell component and is culturing therein methanogenic microorganisms thereby producing methane;
a second apparatus for commingling a portion of the gas flow comprising carbon dioxide from the first apparatus with the circulating liquid medium of the electromethanogenic half-cell component;
a third apparatus for conveying electrons from the photosynthetic half-cell component to the electromethanogenic half-cell component; and
a fourth apparatus for conveying protons from the photosynthetic half-cell component to the electromethanogenic half-cell component;
a fifth apparatus for receiving oxygen produced in the photosynthetic half-cell component; and
a sixth apparatus for receiving methane produced in the methanogenic half-cell component.

2. The system of claim 1, wherein the photosynthetic microorganisms form an electrically-conductive biofilm on the electron-conductive anode.

3. The system of claim 1, wherein the photosynthetic microorganisms are a cyanobacterial culture.

4. The system of claim 3, wherein the cyanobacterial culture is one of a *Synechococcus* sp., a *Synechocystis* sp., a *Prochlorococcus* sp., a *Anabaena* sp., a *Nostoc* sp., or a *Trichodesmium* sp.

5. The system of claim 1, wherein the methanogenic microorganisms form an electrically-conductive biofilm on the electron-conductive cathode.

6. The system of claim 1, wherein the methanogenic microorganisms are a mesophilic methanogenic microbial culture or a thermophilic methanogenic microbial culture.

7. The system of claim 5, wherein the methanogenic microorganisms are a culture of one of a *Methanobacteriales* sp., a *Methanococcales* sp., a *Methanomicrobiales* sp., a *Methanosarcinales* sp., or a *Methanopyrales* sp.

8. The system of claim 1, wherein the light-receiving element comprises an integral component of the photosynthetic half-cell component and/or an external integral component of the photosynthetic half-cell component.

9. The system of claim 8, wherein the light-receiving element is one of a transparent material, a holographic planar concentrator film, a reflector material, a Fresnel lens collector and a total internal reflection film.

10. The system of claim 1, wherein the light-transmitting element is an integral component of the photosynthetic half-cell component.

11. The system of claim 10, wherein the light-transmitting element is a photonic guidance device.

12. The system of claim 9, wherein the photonic guidance device is one of a light waveguide, a fiber optic cable, reflector, a lens, and a light monitoring device.

13. The system of claim 1, wherein the ionic separator is one of a proton exchange membrane, a cation exchange membrane, an anode exchange membranes, an ultrafiltration membrane, and a salt bridge.

* * * * *